(12) United States Patent
U et al.

(10) Patent No.: US 7,090,668 B1
(45) Date of Patent: Aug. 15, 2006

(54) TIME-RELEASED SUBSTANCE DELIVERY DEVICE

(75) Inventors: Hoi Sang U, Rancho Santa Fe, CA (US); James Peter Amis, Encinitas, CA (US)

(73) Assignee: Cytori Therapeutics, Inc., San Diego, CA (US)

( * ) Notice: Subject to any disclaimer, the term of this patent is extended or adjusted under 35 U.S.C. 154(b) by 593 days.

(21) Appl. No.: 10/129,214

(22) PCT Filed: Oct. 27, 2000

(86) PCT No.: PCT/US00/29739

§ 371 (c)(1),
(2), (4) Date: Oct. 21, 2002

(87) PCT Pub. No.: WO01/32068

PCT Pub. Date: May 10, 2001

Related U.S. Application Data

(60) Provisional application No. 60/162,590, filed on Oct. 29, 1999.

(51) Int. Cl.
*A61K 9/22* (2006.01)

(52) U.S. Cl. .................................... 604/892.1; 606/60
(58) Field of Classification Search ...........................
604/288.01–288.04, 891.1; 606/76–77
See application file for complete search history.

(56) References Cited

U.S. PATENT DOCUMENTS

| | | | |
|---|---|---|---|
| 5,618,286 A * | 4/1997 | Brinker | 606/60 |
| 5,800,421 A | 9/1998 | Lemelson | |
| 5,904,934 A | 5/1999 | Maruyama et al. | |
| 5,968,047 A | 10/1999 | Reed | |
| 2003/0139811 A1* | 7/2003 | Watson et al. | 623/11.11 |
| 2005/0021084 A1* | 1/2005 | Lu et al. | 606/218 |

* cited by examiner

*Primary Examiner*—LoAn H. Thanh
(74) *Attorney, Agent, or Firm*—Stout, Uxa, Buyan & Mullins, LLP

(57) ABSTRACT

An implantable, time-released substance delivery device includes a casing having an exterior surface, and a number of pores disposed on the exterior surface of the casing. The time-released substance delivery device further has an interior chamber disposed within the casing, and a number of excretion tubes disposed within the casing. Each of the excretion tubes fluidly connects the interior chamber to one of the pores.

33 Claims, 3 Drawing Sheets

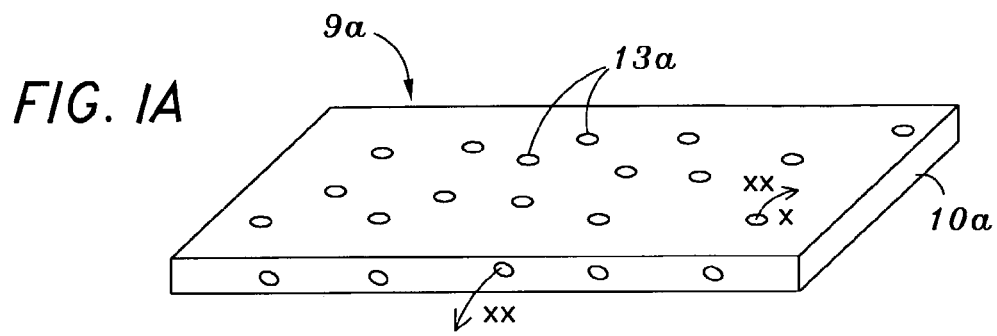
FIG. 1A
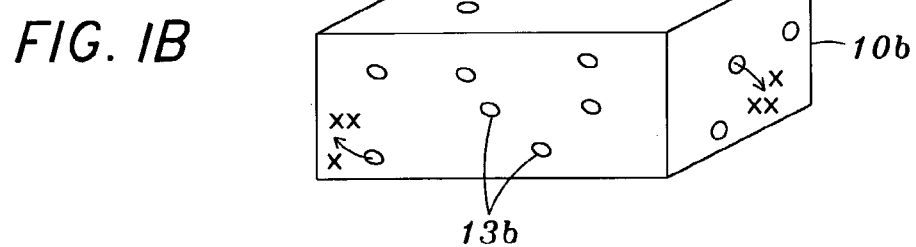
FIG. 1B
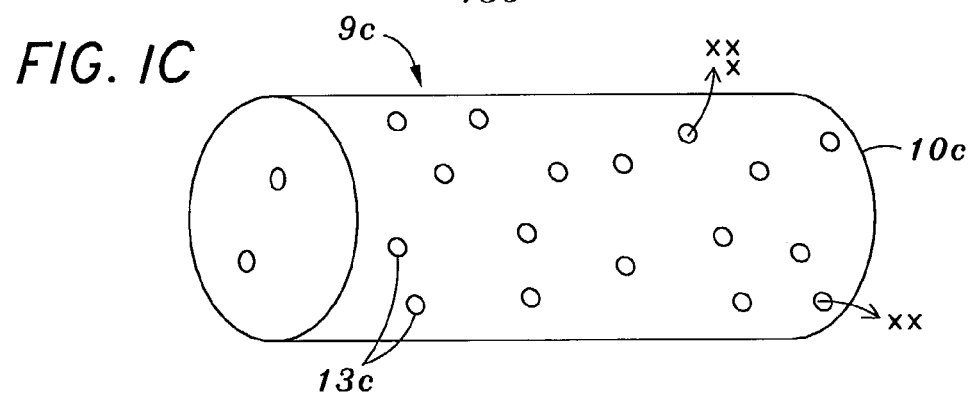
FIG. 1C
FIG. 1D
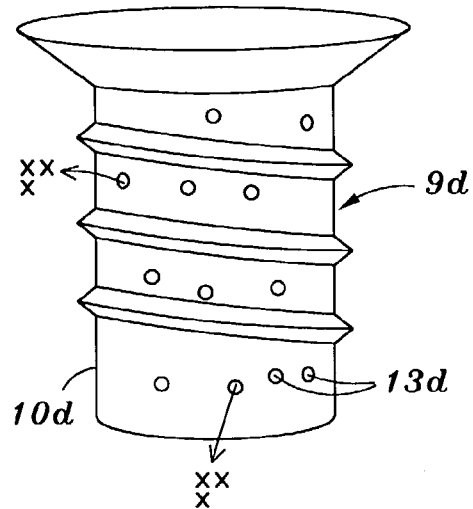

TIME-RELEASED SUBSTANCE DELIVERY DEVICE

This application claims the benefit of U.S. Provisional Application No. 60/162,590, filed Oct. 29, 1999 and entitled TIME-RELEASED SUBSTANCE DELIVERY DEVICE, the contents of which are expressly incorporated herein by reference.

BACKGROUND OF THE INVENTION

1. Field of the Invention

The present invention relates generally to medical implants and, more particularly, to medical implants for providing a time-released delivery of drugs.

2. Description of Related Art

A medicinal substance can be administered to a patient systemically or locally. A systemically administered medicinal substance enters into the blood stream, travels throughout the body, and, hopefully, reaches the part of the patient's body in need of treatment at an effective dose before being degraded by metabolism and excreted. The systemic administration of medicinal substances can be achieved by oral application (e.g., syrups, tablets, capsules and the like), needle injection, transdermal delivery (e.g., a medicinal substance incorporated into a skin patch), and subdermal delivery (e.g., a medicinal substance formulation in a matabolizable matrix placed beneath the skin to release, for example, nicotine or birth control drugs). Systemically delivered medicinal substances can be inefficient, when only a small amount of the administered dose reaches its site of therapeutic action. Moreover, with systemic delivery a medicinal substance can enter parts of the body where it can actually do harm or produce a noxious side effect.

Medicinal substances can be delivered locally by injection (e.g., injection of anesthetic into a patient's gums) or topically (e.g., creams, ointments, and sprays). Although the local delivery of medicinal substances can in some instances overcome the problems of dilution and migration, local medicinal substance delivery can be difficult in certain cases, leaving systemic administration as the viable alternative. Even when local delivery of medicinal substances to a target site is possible, an important consideration still remains of maximizing the therapeutic effectiveness of the local drug delivery by controlling the proper dose and duration of the local delivery of the medicinal substance.

SUMMARY OF THE INVENTION

In order to maximize the therapeutic effectiveness of a medicinal substance at a target site within an organism, which is preferably a human patient, the delivered substance must be applied to the target site in the proper dose amount and for the proper duration. As used herein, a dose is defined as an amount of substance delivered per time, and a duration is defined as a period of time from an initial dose to a final dose. The present invention relates to improved apparatuses, systems and methods for achieving delivery of substances in specified doses and durations to target sites. In particular, a device having a casing with medicinal substances stored in an interior chamber, which is open to the exterior surface via excretion tubes, is disclosed. Modifications are possible for achieving specific doses and durations of substance delivery to maximize the therapeutic effectiveness of the substance.

The present invention, together with additional features and advantages thereof, may best be understood by reference to the following description taken in connection with the accompanying illustrative drawings.

BRIEF DESCRIPTION OF THE DRAWINGS

FIG. 1A illustrates a time-released substance delivery device formed in the shape of a plate or panel, in accordance with an embodiment of the present invention;

FIG. 1B illustrates a time-released substance delivery device formed in the shape of a block, in accordance with an embodiment of the present invention;

FIG. 1C illustrates a time-released substance delivery device formed in the shape of a cylinder, in accordance with another embodiment of the present invention;

FIG. 1D illustrates a time-released substance delivery device formed in the shape of a screw, in accordance with yet another embodiment of the present invention;

DETAILED DESCRIPTION OF THE PRESENTLY PREFERRED EMBODIMENTS

Figure 2:
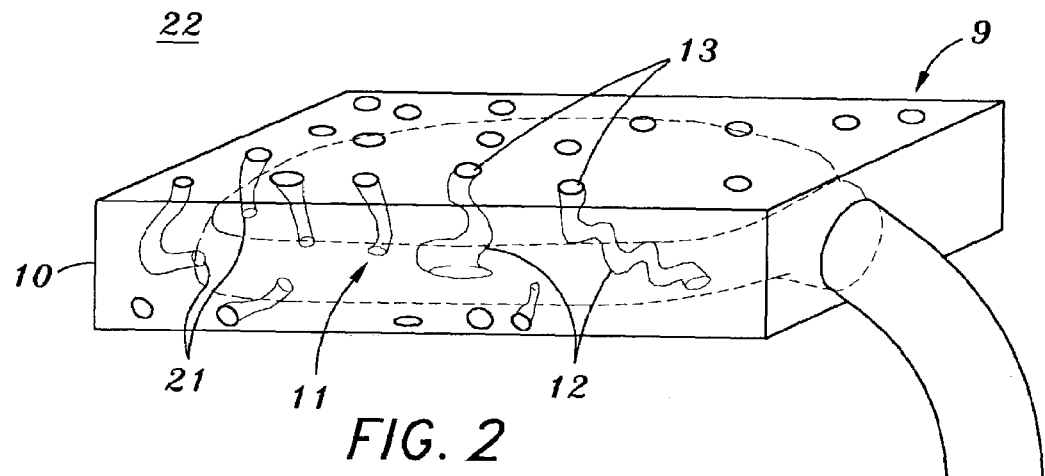
FIG. 2 illustrates a time-released substance delivery device having an access tube that feeds into an internal chamber of the substance delivery device, in accordance with an embodiment of the present invention.

Referring more particularly to the drawings, FIG. 1A illustrates a time-released substance delivery device 9a, which in accordance with the present invention is implanted at or near a target area to be treated. The substance delivery device 9a comprises a casing 10a and a plurality of pores 13a. In the illustrated embodiment, the shape of the device is defined by the casing 10a. Once implanted, the substance delivery device 9a delivers medicinal substances X to the target site by releasing through the pores 13a the medicinal substances X contained within the substance delivery device 9a in the dose and duration specified. A substance delivery device 9b defined by a block-shaped casing 10b having pores 13b is shown in FIG. 1B, and a substance delivery device 9c defined by a cylinder-shaped casing 10c having pores 13c is shown in FIG. 1C. The substance delivery devices of FIGS. 1A, 1B and 1C can be inserted into or secured to an organ or a deep tissue for local treatment, or can be implanted under a derma, for example, for systemic treatment.

In accordance with the present invention, the casings forming the substance delivery devices of the present invention may comprise structures for insertion and implantation into or on organs or tissue, such as in FIGS. 1A, 1B and 1C or, alternatively, may comprise structural or physically functional shapes. For example, the casing may be formed into a plate, mesh, or other fixation, holding, or containment member. In the case of a bone plate or mesh, for example, the substance delivery device can be formed with screw or tack apertures disposed therein. As is known in the art, screw or tack apertures are typically formed in bone plates and meshes to accommodate screws or tacks for securing the bone plate or mesh to bone. Alternatively, the screw or tack apertures may be drilled into the substance delivery device just prior to or during implantation of the substance delivery device.

The shape of the plate, mesh, or other fixation, holding, or containment member may comprise any conventional shape for a such a plate or mesh, with the improvement being the addition of pores and an optional chamber 11 (FIG. 2), in accordance with the present invention. The plate, mesh, or other fixation, holding, repairing, or containment member may be constructed for implantation on or in connection with, for example, muscle, cartilage, tendons, ligaments, connective tissues, blood vessels, bone, and other tissue and organ sites. In the case of a bone plate or mesh, for example, the bone plate or mesh may be formed to have slightly larger dimensions to maintain adequate fixation properties, especially, for example, if the bone plate or mesh is formed of a relatively soft plastic or absorbable material.

In the example of a bone plate or mesh, the bone plate or mesh may be placed over a defective bone area to provide mechanical, reconstructive, protective and/or fixation functions, while simultaneously releasing medicinal substances X to facilitate the bone healing process. The medicinal substances X may comprise, in this example, chemotactic substances for influencing cell-migration, inhibitory substances for influencing cell-migration, mitogenic growth factors for influencing cell proliferation, growth factors for influencing cell differentiation (e.g. insulin-like growth factor, transforming growth factor-beta, fibroblast growth factor, platelet-derived growth factor), and factors for promoting neoangiogenesis (formation of new blood vessels).

A substance delivery device $9d$, having a screw-shaped casing $10d$ with pores $13d$, is shown in FIG. 1D. In the functional-casing embodiment of FIG. 1D, the casing $10d$ can serve as both a fastener and a substance delivery device $9d$. For example, the substance delivery device $9d$ may be constructed according to the principles set forth above, in connection with a substance delivery device formed into a bone plate or mesh, and may be used to secure, for example, bone plates or meshes to bone. Although specific embodiments of functional casings in the form of bone plates, meshes, and screws have been discussed, other embodiments, which would allow for the casing to be functional, for example, are also contemplated to be within the scope of the present invention. For example, substance delivery devices may be formed to operate, inter alia, as soft tissue tacks or spinal rods.

The casings may be constructed from non-biodegradable or biodegradable material. For biodegradable casings, a preferred embodiment comprises a biodegradable casing that degrades only after all of the medicinal substances X therewithin have been depleted. Alternatively, other embodiments of the casing may partially or completely degrade before the depletion of the medicinal substances X contained therein, thereby achieving non-linear releases of the medicinal substances X.

In turn, the aforementioned casings may also be embedded in other implant devices, for example. These other implant devices can be biodegradable, so that when they degrade, the time-released substance delivery devices are exposed to the target site to thereby achieve predetermined releases of the medicinal substances X beginning at a delayed point in time.

Figure 3:
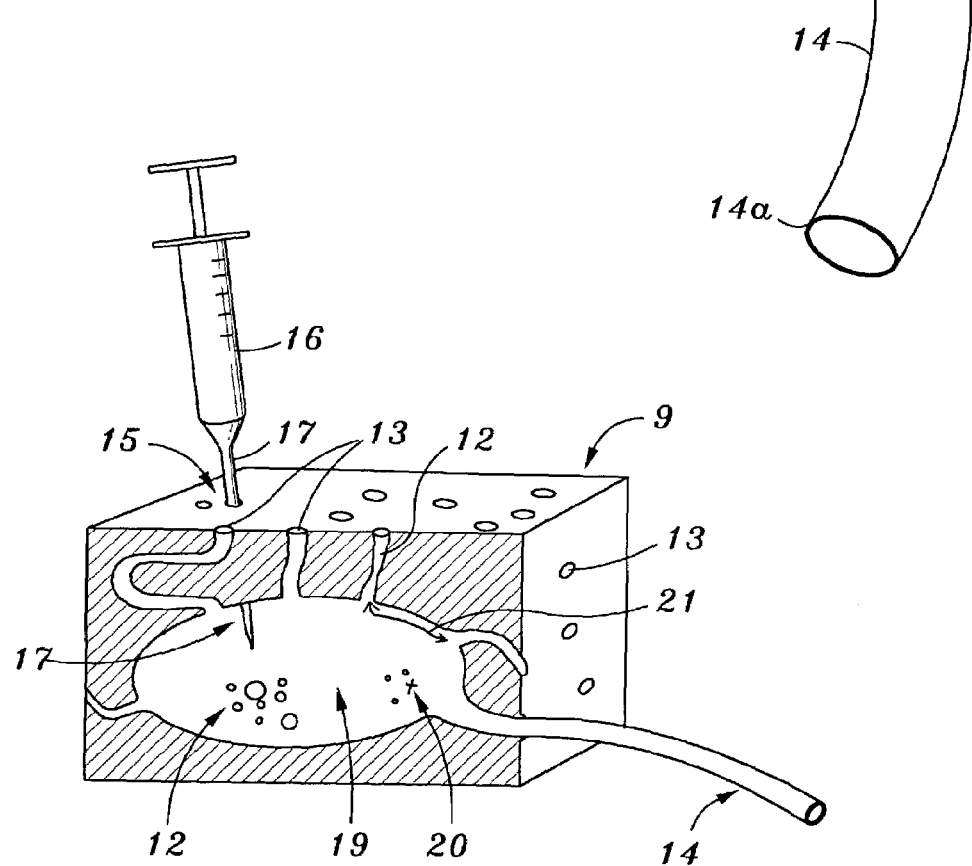
FIG. 3 illustrates a time-released substance delivery device having a perforable membrane and an access tube fluidly connected to an internal chamber of the substance delivery device, in accordance with another embodiment of the present invention.

Referring now to FIGS. 2 and 3, in a preferred embodiment the substance delivery device 9 comprises a casing 10 and a chamber 11. The substance delivery device 9 further comprises a set of excretion tubes 12 that fluidly connect the exterior surface of the casing 10 to the interior chamber 11, resulting in a set of pores 13 and a set of interior open ends 21, respectively. Preferably, at least one side or portion of the casing 10 comprises a perforable membrane 15, as shown in FIG. 3, so that a needle 17 and syringe 16 can be used to fill the substance delivery device 9 with, for example, medicinal substances X. In accordance with the present invention, the needle 17 can be used to fill the chamber 11 before and/or after implantation of the substance delivery device into tissue. For example, the chamber 11 may be filled with a medicinal substance X before implantation and, subsequently, refilled to maintain an ongoing, controlled delivery of the medicinal substance X and/or other substances to the target site.

Operationally, doses and durations are functions of the sizes, shapes and number of excretion tubes 12 and the concentration of medicinal substance X in the chamber 11. For example, if a low dose is desired, a substance delivery device 9 with narrow excretion tubes 12 can be selected to physically limit the diffusion rate of the medicinal substance X from the interior chamber 11 to the exterior pores 13. Since fewer molecules of medicinal substance X per time reach the exterior pore 13 under this condition, lower amounts of medicinal substance X are delivered to the targeted site per time, resulting in lower dosage delivery. Furthermore, the number of individual excretion tubes 12 in the substance delivery device 9 can directly affect the dosage delivery. For example, a fewer number of excretion tubes 12 effectively decreases the number of channels available for the outward diffusion of the medicinal substance X contained in the chamber 11, thereby decreasing the dosage to the target site. Also, the concentration of the medicinal substance X in the chamber 11 contributes to the dose. For example, low concentrations of medicinal substance X in the chamber 11 results in low gradient pressure, which in turn results in fewer molecules diffusing from inside the chamber 11 to the exterior pores 13 per time, which ultimately results in a lower dosage delivery.

The duration of delivery is also a function of the size and number of the excretion tubes 12 and the concentration of medicinal substance X in the chamber 11. For example, smaller excretion tubes 12 decrease the amount of medicinal substance X released per time. Because the medicinal substance X is released slowly, it takes longer to deplete the medicinal substance X in the chamber 11, and therefore, the duration of the medicinal substance X release is increased. For the same reason, if there is a high amount of medicinal substance X in the chamber 11 initially, the duration can be increased.

By applying conventional kinetic models and calculations, the resultant effect of size, shape, number and distribution of excretion tubes 12 and amount of substance X in the chamber 11 on dose and duration can be tabulated. Therefore, a system of the present invention may preferably comprise a lookup table, one or more medicinal substances X, a needle capped syringe 16 and 17, and a substance delivery device 9.

In practice, a method for using the substance delivery device 9 involving the following steps may be employed by a physician. First, the physician diagnoses and determines the appropriate dose and duration for treatment of a certain medical condition. The physician may then use the lookup table to select the substance delivery device 9 with the appropriate number and size of excretion tubes 12 and the amount of medicinal substance X needed in the chamber 11.

Subsequently, the physician can use a syringe 16 and 17 to inject the appropriate medicinal substance X into the chamber 11. After the chamber 11 is loaded, the physician may surgically implant the substance delivery device 9 into the patient.

After the medicinal substance X is partially or fully depleted from the chamber 11, the physician may return to the location and surgically retrieve the substance delivery device 9. Alternatively, if the substance delivery device 9 is constructed from a biodegradable material, it can be left in the patient's body. If desired, the surgeon may refill the substance delivery device 9 using, for example, a needle while the substance delivery device 9 remains in the patient, as shown in FIG. 3. This in situ refill procedure may be accomplished by, for example, reopening the surgical site, using visual or tactile verification of the location of the substance delivery device, or implementing an imaging technique to ensure that the refill needle finds its way into the chamber 11.

In accordance with one embodiment, extended excretion tube lengths are provided in connection with one or more of the excretion tubes 12. Each increased tube length delays the time of excretion of medicinal substance X out of the pore from the time at which the medicinal substance X is placed into the chamber 11. Consequently, the medicinal substance X can be delayed from being released until after the substance delivery device 9 is implanted into the patient, with the delay time being a function of the length and cross-sectional area of the excretion tube, (wherein the excretion tube or passage does not necessarily have a circular cross-sectional area). Moreover, partial barriers and/or flow restrictions, enhancers, channelers or directors may be formed and placed within at least a portion of one or more of the excretion tubes 12. The substance delivery device 9 with such a delay mechanism, for example, may be used when it is medically indicated that the medicinal substance X should be released at sometime after the time-released substance delivery device 9 is implanted. Furthermore, an alternative system may comprise a substance delivery device 9 with such a delay mechanism and a substance delivery device 9 (or a set of substance delivery devices) that release medicinal substance X immediately or shortly after implantation. Such a system when used can produce certain dosage and duration combinations, such as those specifying immediate and/or delayed releases.

Figure 4A:
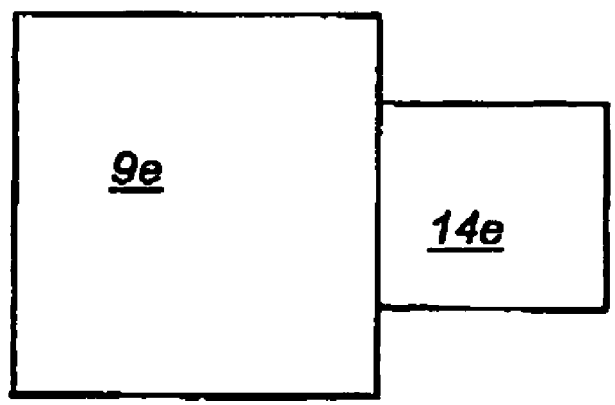
FIG. 4A is a block-diagram depiction of a time-released substance delivery devices in the form of a screw with a interconnected access tube, in accordance with an embodiment of the present invention.
Figure 4B:
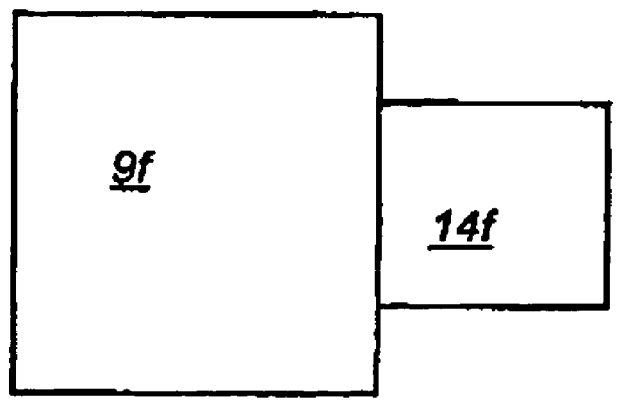
FIG. 4B shows in block-diagram format a time-released substance delivery device constructed as a tack with a connected access tube, in accordance with another embodiment of the present invention.

As exemplified in FIGS. 2 and 3, another embodiment in accordance with the present invention includes an access tube 14 that feeds directly into the chamber 11. A purpose of this access tube 14 is to allow access into the chamber 11, for example, once the substance delivery device 9 has been implanted. In accordance with one preferred embodiment, the access tube 14 comprises a perforable membrane, disposed at or near its end 14a, and suitable for being pierced by a needle for delivery of fluids therethrough and into the chamber 11. FIGS. 4a and 4b schematically represent other examples of time-released substance delivery devices with access tubes feeding into internal chambers. More particularly, FIG. 4A is a block-diagram depicting a time-released substance delivery device 9e in the shape of a screw with an interconnected access tube 14e, and FIG. 4B is a block-diagram showing a time-released substance delivery device 9f configured as a tack coupled with an access tube 14f.

The substance delivery device 9 may be constructed with a needle 17 access (e.g., a perforable membrane 15) to the chamber 11 and/or with an access tube 14 fluidly connected to the chamber 11. The chamber 11 may initially be filled with a saline solution and/or other biocompatible fluid (e.g., a medicinal substance X such as an anesthetic) wherein the user (using, for example, a needle) can introduce a fluid through a needle 17 access (e.g., a perforable membrane 15) and/or through the access tube 14 and into the chamber 11 to thereby displace (and/or expedite excretion of), and/or dilute or modify, the biocompatible fluid in the chamber 11. In modified embodiments the perforable membrane of the access tube 14 may comprise a locking-type connector for receiving a corresponding external substance-introducing tube with a matching or mating connector.

When the substance delivery device 9 is implanted, the end 14a of the access tube 14 may be positioned to extend out of the dermis for subsequent access. In a modified embodiment, the end 14a of the access tube 14 may extend below the dermis of the patient so that the skin is breached only when the user desires to introduce external fluids (e.g., medicinal substances X) into the access tube 14. If, for example, the end 14a is just below the dermis, the surgeon can visually or tactilely locate the end 14a beneath the patient's dermis. For example, the substance delivery device 9 may be implanted deep within an organ with the access tube extending out of the organ and terminating just beneath the patient's dermis.

For a chemotherapy treatment, for example, a biodegradable substance delivery device 9 may be implanted within tissue or an organ, such as the brain, with the access tube extending through the skull and terminating just beneath the patient's dermis.

Imaging techniques, such as Magnetic Resonance Imaging (MRI) can be used to accurately implant the substance delivery device 9 in close proximity to or within a target site such as a tumor. In accordance with a preferred embodiment, the substance delivery device will comprise a biodegradable (e.g., a resorbable polymer based material) or non-scatterable material for this operation. Once the access device has been implanted, the surgeon can then access the chamber 11 using an a needle 17/perforable membrane 15 and, (optionally, using the above-referenced imaging techniques) and/or an access tube 14, to introduce, for example, chemotherapy medicinal substances X to the tumor location or target site.

One reason for accessing the chamber 11 is to replenish the chamber 11 with more of the same medicinal substance X or other medicinal substances X during the course of treatment. In a modified embodiment, the surgeon can access the chamber 11 to remove medicinal substances X from the chamber with suction. In yet another modified embodiment, the surgeon can apply suction to the access tube 14 and/or to a needle 17/perforable membrane 15, to draw body fluids from the extracellular space 22 through the excretion tubes 12 and into the chamber 11 and, subsequently, out of the chamber 11 through either the needle 17/perforable membrane 15 and/or the access tube 14.

Another reason for accessing the chamber 11 in situ is to introduce reagent that would activate or deactivate one or more medicinal substances X already contained in the chamber 11. The access tube 14 and/or needle 17/perforable membrane 15 can allow for a higher degree of flexibility during the course of treatment. Furthermore, another system in accordance with the present invention may comprise a substance delivery device 9 and a plurality of medicinal substances X. With the flexibility of introducing a different medicinal substance X to the target area once the substance delivery device 9 is implanted, the system may be employed to treat medical conditions requiring a series of different medicinal substances X over a course of time. Two or more chambers 11 may be formed in a single substance delivery device 9, with one or more of the chambers being engineered to provide a different dose and duration. For example, a second chamber may be provided with fewer excretion tubes connected thereto and/or different types of medicinal substances and/or carriers 18 (discussed, infra) disposed therein.

Yet another embodiment of the present invention includes placement of medicinal substances X contained within a carrier 18 within the chamber 11. A carrier comprises a protective exterior coating and an interior empty volume for storage of one or more medicinal substances X, for example. One or more of these carriers 18 may be constructed larger than one or more of the interior open ends 21 for attenuated or impeded excretion. Thus, in accordance with this embodiment, the medicinal substance X contained therein may only be released upon the degeneration of the carriers 18. In a modified embodiment, carriers, which are larger than some or all of the excretion tubes 12, can be placed within the chamber 11 of an absorbable substance delivery device, in order to attenuate or impede excretion thereof. One effect of these arrangements is to enable a delayed release of medicinal substance X once the substance delivery device 9 is implanted.

Alternatively, the carriers 18 may be constructed sufficiently small so as to enter into the excretion tube 12 and diffuse out of the pores 13 into the extracellular space 22. Once in the extracellular space 22, the carriers 18 may further diffuse away from the substance delivery device 9. One use of this small size carrier is that it can carry (and protect) the medicinal substance X during the diffusion away from the substance delivery device 9 and allow for the medicinal substance X to be effective at some distance away from the substance delivery device 9.

One preferred embodiment of the current invention comprises pores 13 on all sides of the casing 10. This construction allows for a relatively isotropic dispersion of medicinal substance X by the substance delivery device 9. However, an alternative embodiment may restrict the pore surface, for example, to only one side of the casing 10. With the pores 13 present on only one side, it is possible to limit the diffusion of the medicinal substance X to a particular tissue surface at the implant location for focused local delivery of the medicinal substance X.

In terms of manufacturing the substance delivery device 9, it is preferable in accordance with one aspect of the present invention that the chamber 11 remain empty prior to use. It is only at the time of use, or shortly prior thereto, that the medicinal substance X is injected into the chamber 11. However, in an alternative embodiment, the substance delivery device 9 may be filled or impregnated with certain medicinal substances X during the manufacturing process. For example, in accordance with one embodiment of the present invention, part or all of the material of the substance delivery device is impregnated or partially formed with a medicinal substance X, with the existence of the chamber 11 being optional. The substance delivery device 9 may be formed of a material that degrades over time after implantation so that degradation of all or part of the substance delivery device 9 results in the release of the medicinal substance X. The pores 13 in accordance with this embodiment provide additional surface area for such degradation and consequential delivery of the medicinal substance X.

While the foregoing preferred embodiments of the invention have been described, various alternatives, modifications, and equivalents other than the ones already discussed may be used. For example, a substance delivery device 9 may have a set of short and large excretion tubes 12 for immediate release of substance A after the implantation of the substance delivery device 9. Concurrently, the substance delivery device 9 may also have substance B contained in large carriers 18 located in the chamber 11. Because of their sizes, as discussed above, these carriers 18 remain trapped in the chamber 11 for a period of time and are subsequently released upon degradation. The overall effect of this particular substance delivery device 9 is that it is able to release substance A shortly after implantation and delay the release of substance B. Along this line of construction of the apparatus and/or systems, it is possible to engineer an apparatus and/or substance delivery device 9 that is tailored to the treatment specifications of various medical conditions. For example, a device can be engineered to release 25% of the chamber 11 contents within three months of implantation, 50% within the first year, and the remaining contents within the next two years.

As used herein the term "medicinal substance" includes, but is not limited to, analgesics, local anesthetics, antibiotics, steroids, anti-tumor agents, hormones, and hormone-like agents. Examples of antibiotics useful with the present invention include, but are not limited to: ampicillin, chloramphenicol, chlortetracycline, clindamycin, erythromycin, gramicidin, gentamicin, mupiroicin, neomycin, polymyxin B, bacitracin, silver sulfadiazine, tetracycline and chlortetracycline. Those of ordinary skill in the art will appreciate that there are other appropriate topical antibiotics, such as those listed in U.S.P.D., which may also be used in the present invention. Examples of hormones and other related drugs useful with the present invention include, but are not limited to: human growth hormone (HGH), bone morphogenetic proteins (BMPs) (C. F. Paatsama, S., et al.) transforming growth factors (TGF-.beta.s), interferons, interleukins, calcitonin, estrogen and 17-.beta. estradiols. Examples of anti-inflammatory drugs include, but are not limited to: cortisone, Nonsteroidal Anti-inflammatory Drugs (NSAIDs), and interleukin 3 inhibitors. Many of the anti-tumor drugs in current clinical use are cytotoxic materials, which work by killing the malignant cells faster than the normal cells.

Although an exemplary embodiment of the invention has been shown and described, many other changes, modifications and substitutions, in addition to those set forth in the above paragraphs, may be made by one having ordinary skill in the art without necessarily departing from the spirit and scope of this invention.

The invention claimed is:

1. An implantable, time-released substance delivery device, comprising:
   a casing having an exterior surface;
   an access tube connected to and extending away from the exterior surface of the casing;
   a plurality of pores disposed on an exterior surface of the substance deliver device:
   an interior chamber enveloped by the substance delivery device, wherein the enveloped interior chamber is constructed to hold a substance and wherein the substance delivery device is formed of a non-corrosive material;
   a perforable membrane, which when punctured by a needle will subsequently re-seal to maintain a fluid barrier, wherein the perforable membrane is constructed to facilitate multiple penetrations by a needle therethrough and into the interior chamber while maintaining a fluid seal after each penetration; and
   plurality of excretion tubes disposed within the casing, each of the plurality of excretion tubes fluidly connecting the interior chamber to one of the plurality of pores.

2. The time-released substance delivery device as set forth in claim 1, wherein the substance delivery device comprises an absorbable material.

3. The time-released substance delivery device as set forth in claim 1, wherein the substance delivery device comprises a non-scatterable material that will not substantially scatter incident imaging beams.

4. The time-released substance delivery device as set forth in claim 1, wherein the substance delivery device has dimensions suitable for being implanted beneath the skin of a patient.

5. The time-released substance delivery device as set forth in claim 1, wherein the substance delivery device has dimensions suitable for being implanted within an organ of a patient.

6. The time-released substance delivery device as set forth in claim 1, wherein the substance delivery device is formed into one of a tack and a screw.

7. The time-released substance delivery device as set forth in claim 1, wherein the substance delivery device comprises an absorbable material that is formed into one of a tack and a screw.

8. The time-released substance delivery device as set forth in claim 1, wherein the substance delivery device is formed into a bone plate.

9. The time-released substance delivery device as set forth in claim 1, wherein the substance delivery device comprises an absorbable material that is formed into a bone plate.

10. The time-released substance delivery device as set forth in claim 1, wherein the interior chamber comprises a medicinal substance.

11. The time-released substance delivery device as set forth in claim 1, wherein the substance delivery device is impregnated with a medicinal substance.

12. The time-released substance delivery device as set forth in claim 1, wherein the access tube is in fluid communication with the internal chamber.

13. The time-released substance delivery device as set forth in claim 12, wherein the access tube comprises a first end and a second end, the first end being connected to the exterior surface of the casing and the second end being located opposite the first end.

14. The time-released substance delivery device as set forth in claim 13, wherein the interior chamber comprises a medicinal substance.

15. The time-released substance delivery device as set forth in claim 13, wherein the second end of the access tube comprises a perforable membrane fluidly isloating an interior of the access tube from an exterior surface of the access tube.

16. The time-released substance delivery device as set forth in claim 13, wherein a distance between the first end and the second end of the access tube is greater than a maximum width of the casing.

17. The time-released substance delivery device as set forth in claim 2, wherein the interior chamber comprises a medicinal substance.

18. The time-released substance delivery device as set forth in claim 6, wherein the interior chamber comprises a medicinal substance.

19. The time-released substance delivery device as set forth in claim 8, wherein the interior chamber comprises a medicinal substance.

20. The time-released substance delivery device as set forth in claim 2, wherein the substance delivery device is impregnated with a medicinal substance.

21. The time-released substance delivery device as set forth in claim 6, wherein the substance delivery device is impregnated with a medicinal substance.

22. The time-released substance delivery device as set forth in claim 8, wherein the substance delivery device is impregnated with a medicinal substance.

23. The time-released substance delivery device as set forth in claim 1, wherein the time-released substance delivery device is constructed to be implanted to deliver a systemic treatment.

24. The time-released substance delivery device as set forth in claim 2, wherein the time-released substance delivery device is constructed to be implanted on in connection with one or more of an organ, muscle, cartilage, tendon, ligament, connective tissue, blood vessel and bone.

25. The time-released substance delivery device as set forth in claim 1, wherein the time-released substance delivery device comprises one or more of an analgesic, an anesthetic, an antibiotic, a steroid, an anti-tumor agent, a hormone and a hormone-like agent.

26. The time-released substance delivery device as set forth in claim 1, wherein the time-released substance delivery device comprises one or more of a substance for influencing cell-migration, a substance for influencing cell proliferation, a substance for influencing cell differentiation and a substance for promoting neoangiogenesis.

27. The time-released substance delivery device as set forth in claim 1, wherein the time-released substance delivery device comprises a structure with an exterior coating and an interior volume.

28. The time-released substance delivery device as set forth in claim 1, wherein the casing is embedded in another implant device.

29. The time-released substance delivery device as set forth in claim 28, wherein the time-released substance delivery device comprises an absorbable material.

30. The time-released substance delivery device as set forth in claim 28, wherein the other implant device is biodegradable, so that when the other implant device degrades at least a part of the time-released substance delivery device is exposed.

31. The time-released substance delivery device as set forth in claim 30, wherein the time-released substance delivery device comprises an absorbable material.

32. The time-released substance delivery device as set forth in claim 30, wherein exposure of the time-released substance delivery device causes the time-released substance delivery device to deliver a substance.

33. The time-released substance delivery device as set forth in claim 32, wherein the time-released substance delivery device comprises an absorbable material.

* * * * *